United States Patent [19]

Popp et al.

[11] Patent Number: 5,118,603
[45] Date of Patent: Jun. 2, 1992

[54] PROCESS FOR INACTIVATION OF RECOMBINANT DNA

[75] Inventors: Friedrich Popp, Sindelsdorf: Michael J. Comer; Günther Schumacher, both of Bernried; Michael J. Munster, Penzberg; Bodo Seydler, Weilheim, all of Fed. Rep. of Germany

[73] Assignee: Boehringer Mannheim GmbH, Mannheim, Fed. Rep. of Germany

[21] Appl. No.: 363,887

[22] PCT Filed: Jul. 4, 1988

[86] PCT No.: PCT/EP88/00592
§ 371 Date: Jun. 1, 1989
§ 102(e) Date: Jun. 1, 1989

[87] PCT Pub. No.: WO89/03226
PCT Pub. Date: Apr. 20, 1989

[30] Foreign Application Priority Data
Oct. 7, 1987 [DE] Fed. Rep. of Germany ....... 3733921

[51] Int. Cl.⁵ .................. C07H 1/00; C07H 21/04
[52] U.S. Cl. ............................ 435/6; 536/27
[58] Field of Search ............. 435/6; 536/27, 28, 29; 560/318; 562/1, 2; 568/558-560

[56] References Cited

U.S. PATENT DOCUMENTS

| | | | |
|---|---|---|---|
| 798,013 | 8/1905 | Smith et al. | 562/2 |
| 2,058,315 | 10/1936 | Huttenhocher et al. | 561/1 |
| 2,536,008 | 12/1950 | Rust et al. | 580/318 |
| 2,802,025 | 8/1959 | Weitbrecht et al. | 562/2 |
| 2,957,931 | 10/1960 | Hamilton et al. | 568/560 |
| 4,225,451 | 9/1986 | McCrudden et al. | 252/99 |

OTHER PUBLICATIONS

The Merck Index, Ninth Edition, 1976, pp. 6948, 6949, and 4695.
Morrison and Boyd, Organic Chemistry Fourth Edition Allyn and Bacon, Inc., Boston, pp. 382-383.
The Merck Index (1989) Eleventh Edition, p. 1134.
Kirk-Othmer Concise Encyclopedia of Chemical Technology, pp. 845-850.

*Primary Examiner*—Ronald W. Griffin
*Assistant Examiner*—Gary L. Kunz
*Attorney, Agent, or Firm*—Felfe & Lynch

[57] ABSTRACT

A method of inactivating the biological activity of natural or recombinant DNA in a biomass, by adding a percarboxylic acid containing 1 to 3 carbon atoms, one of its salts, an alkali metal peroxide, or an alkali metal peroxomonosulfate and subsequently heating the mixture to 60° to 100° C.

6 Claims, 4 Drawing Sheets

60 Min./RT  30 Min./80°C

PROCESS FOR INACTIVATION OF RECOMBINANT DNA

DESCRIPTION

The invention concerns a process for the inactivation of the biological activity of DNA, especially recombinant DNA.

According to the directions for the protection against danger due to in vitro newly combined nucleic acids, which have been published by Federal Minister for Research and Technology, wastes which contain nucleic acids, thus DNA, are to be sterilised or denatured. Therefore, in the case of working with recombinant DNA-containing micro-organisms, it is not only necessary to inactivate the organisms but also to destroy the possibly recombinant DNA in the organisms. As a rule, the killing off of micro-organisms takes place relatively simply. However, the DNA in the micro-organisms is, as a rule, not destroyed by the measures employed. Since, now, this sterilisation or denaturing must take place before the biomass is introduced into the clarification plant, measures are, furthermore, to be carried out in order that no substances get into the subsequent clarification plant with the biomass which, for example, damage or kill off the micro-organisms of the activated sludge if a biological clarification plant according to the activated sludge process is supplied, which is preferred. Thus, care must be taken that the substances used are not toxic or, before introduction into the clarification plant, are so broken down that they can cause no harm.

The methods previously known and recognized e.g. by the Federal Ministry of Health (BGA) of the Federal Republic of Germany and by the Central Commission for Biologicial Safety (ZkBS) of the Federal Republic of Germany for the sterilization and inactivation (e.g. steam sterilisation over 20 min. at 121° C.) are very expensive. Especially in the case of the treatment of industrially usual fermentation amounts of 10 to 50 m$^3$, these processes are very cost intensive not only for apparatus but also because of the high energy consumption.

Therefore, it was the task of the present invention to make available a process with which the biological activity of DNA, especially recombinant DNA, can be inactivated with certainty without undesired, especially toxic substances getting into the waste water. Furthermore, the process is to be capable of being carried out cost-favourably.

This task is solved by a process for the inactivation of the biological activity of DNA, especially recombinant DNA, which is cahracterized in that one adds to the DNA-containing biomass a percarboxylic acid with 1 to 3 carbon atoms, an alkali metal peroxide or an alkali metal peroxomonosulphate and heats the mixture then to 60° to 100° C.

Surprisingly, it was ascertained that by means of the use of the above-mentioned compounds and by heating of the batch, not only are still living micro-organisms killed off but that also the DNA contained in them is broken down to such an extent that no fragments capable of replication remain.

With the process according to the invention, a breakdown of the DNA to fragments smaller than/equal to 500 bp can be achieved which is also not exceeded by the waste disposal processes (autoclaving) permitted by the ZKBS. Such fragments are no longer biologically active and can, therefore, be passed without danger into the waste water.

The process according to the invention can be advantageously used for biomasses such as result in the case of the culturing and production of recombinant DNA within or outside of animal or human cells, as well as for micro-organisms. Waste waters which contain micro-organisms, plasmids and the like DNA-containing material can, therefore, before the introduction into the actual clarification plant, be subjected to the pre-treatment according to the invention which ensures that no DNA in a form capable of replication can any longer be present.

The biomass, such as for example a micro-organism-containing culture solution, is mixed with a percarboxylic acid with 1 to 3 carbon atoms, an alkali metal peroxide or an alkali metal peroxomonosulphate, since this is, on the one hand, relatively stable and, on the other hand, is cost-favourable. Performic acid and perpropionic acid are just as suitable. In the scope of the invention, as alkali metal there is preferred Na, K and Li. The ammonium salts are here to be counted with the alkali metal salts. The per compound is preferably added in a concentration of 0.05 to 5 wt. %. The concentration thereby depends upon the compound used, as well as upon the biomass to be treated.

After addition of the per compound, the mixture is heated. An inactivation is achieved by heating to a temperature between 60° and 100° C. It is preferred to heat to a temperature between 70° and 90° C. Especially in the case of the use of peracetic acid, it is advantageous to heat the mixture to at least 70° C. since, in the case of this temperature, the peracetic acid is rapidly completely decomposed.

The heating of the mixture preferably takes place until no DNA with a chain length of more than 500 base pairs is detectable chromatographically. As a rule, this is the case after 20 to 60 minutes. In order to test whether all DNA has been broken down, an aliquot is taken from the mixture and an agarose gel electrophoresis carried out therewith. The chromatographic separation according to molecular weight then shows which fragments are present in the solution.

The process according to the invention is advantageously carried out in the pH range between 6 and 11, especially preferably between pH 7 and 10.

An important advantage of the process according to the invention is that the per compounds used are completely broken down. From the compounds used, there result only biologically harmless and non-toxic compounds which can even be passed directly into the canalisation and in the case of which no danger exists that the micro-organisms contained in the activated sludge are killed off.

The invention is further explained by the following Examples in conjunction with the accompanying drawings of electropherograms.

EXAMPLE 1

Figure 1:
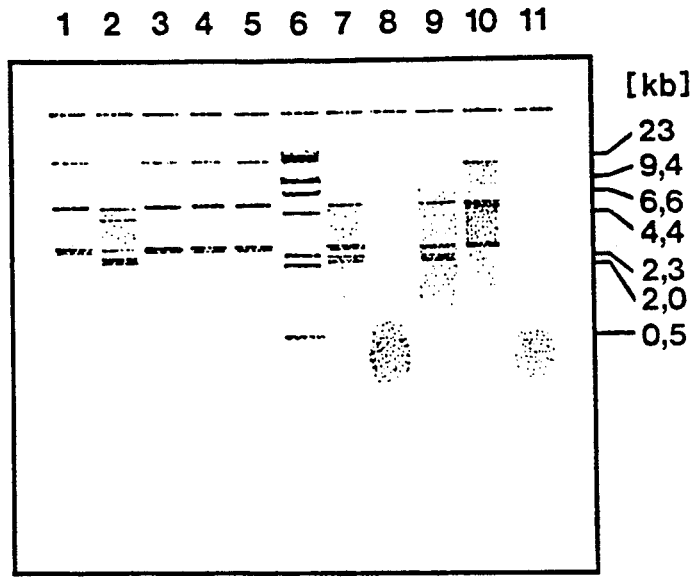
FIG. 1 shows an electropherogram of different samples in which different per compounds have been used (Table 1).
Figure 2:
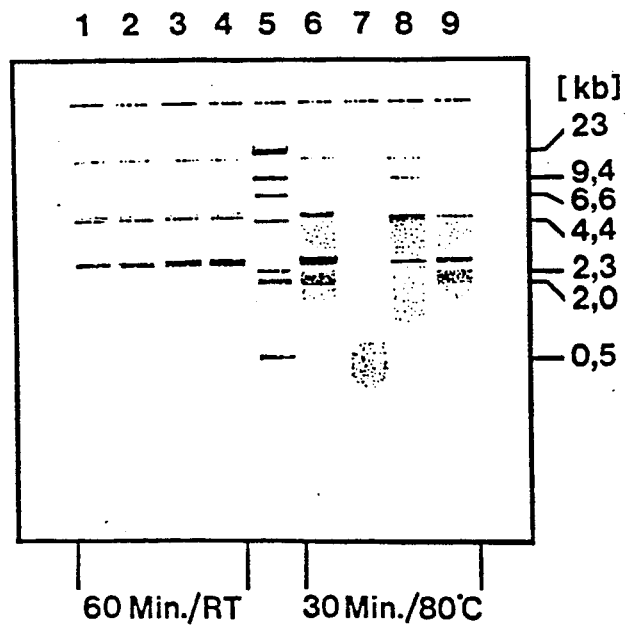
FIG. 2 shows an electropherogram of different samples in which different per compounds have been used (Table 2).

The decomposition of plasmid DNA by per compounds was tested. For this purpose, the plasmid pBR322 (PNAS, USA, 75 (1978) 373) was used. Of this plasmid, solutions were used which contained 30 μg. of plasmid DNA/ml. These samples were treated in different batches with per compounds. 100 μl. of the corresponding batch were incubated under the particular conditions given in the following Tables. Subsequently, in each case, 20 μl. of the batch were taken, mixed with 5 μl. of sample buffer and applied to an agarose gel electrophoresis plate (0.8 wt. % agarose; 0.04 mol/l. TRIS/acetate buffer, pH 8; 0.001 mol/l. EDTA) and separated as stated in Maniatis T., Fritsch E. S. and Sambrook J. in Molecular Cloning, Cold Spring Harbor Laboratory, New York, 11724 (1982), page 454. As comparison solutions were used 0.6 μg. pBR322 in 20 μl. TE buffer and 5 μl. sample buffer. As length standard (λ-length standard) was used phage lambda (J. Mol. Biol. 162 (1982) 729-773), cleaved with Hind III (obtainable as DNA length standard II, Order No. 236 250, Boehringer Mannheim GmbH). The molecular weights of the fragments are: 15.26, 6.21, 4.41, 2.88, 1.53, 1.34, 0.37 megadalton corresponding to 23130, 9416, 6682, 4361, 2322, 2027, 564 base pairs. The per compounds used, concentrations and incubation conditions are to be seen from the following Tables 1 to 5:

TABLE 1

| trace | per compound | temperature/ incubation time |
|---|---|---|
| 1 | — | room temperature (RT)/60 min. |
| 2 | Na-peroxide, 0.1% | " |
| 3 | urea peroxide, 0.1% | " |
| 4 | Na-perborate, 0.1% | " |
| 5 | peracetic acid, 0.1% | " |
| 6 | λ-length standard | — |
| 7 | — | . |
| 8 | Na-peroxide, 0.1% | 80° C./30 min. |
| 9 | urea peroxide, 0.1% | 80° C./30 min. |
| 10 | Na-perborate, 0.1% | 80° C./30 min. |
| 11 | peracetic acid, 0.1% | 80° C./30 min. |

TABLE 2

| trace | per compound | temperature/ incubation time |
|---|---|---|
| 1 | — | room temperature (RT)/60 min. |
| 2 | peracetic acid, 0.1% | " |
| 3 | Perform⁺, 0.1% | " |
| 4 | H₂O₂, 0.1% | " |
| 5 | λ-length standard | — |
| 6 | — | 80° C./30 min. |

TABLE 2-continued

| trace | per compound | temperature/ incubation time |
|---|---|---|
| 7 | peracetic acid, 0.1% | 80° C./30 min. |
| 8 | Perform⁻, 0.1% | 80° C./30 min. |

Perform⁻ is a mixture of 20 parts of potassium peroxomonosulfate, 15 parts of sodium benzoate and 10 parts of tartaric acid and is the product of Schulke and Mayr GmbH, D-2000 Norderstedt, Germany.

TABLE 3

| trace | per compound | temperature/ incubation time |
|---|---|---|
| 1 | — | RT/60 minutes |
| 2 | peracetic acid, 0.5% | " |
| 3 | Perform⁻, 0.5% | " |
| 4 | H₂O₂, 0.5% | " |
| 5 | λ-length standard | " |
| 6 | — | — |
| 7 | peracetic acid, 0.5% | 80° C./30 minutes |
| 8 | Perform⁻, 0.5% | " |
| 9 | H₂O₂, 0.5% | " |

TABLE 4

| trace | concentration peracetic acid (wt. %) |
|---|---|
| 1 | 0% (room temperature) |
| 2 | 0% |
| 3 | 0.9% |
| 4 | 0.5% |
| 5 | 0.1% |
| 6 | 0.05% |
| 7 | 0.025% |
| 8 | λ-length standard |

TABLE 5

| trace | concentration Perform⁻ (peroxomonosulphate (wt. %) |
|---|---|
| 1 | 0% (room temperature) |
| 2 | 0% |
| 3 | 0.9% |
| 4 | 0.5% |
| 5 | 0.1% |
| 6 | 0.05% |
| 7 | λ-length standard |

Figure 3:
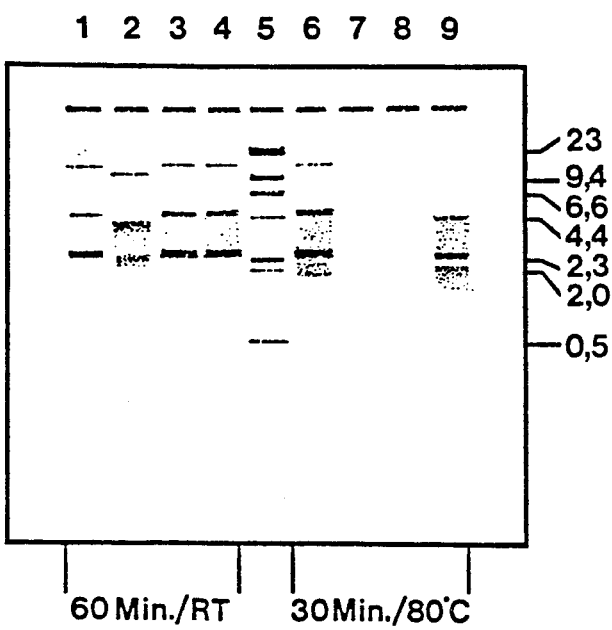
FIG. 3 shows an electropherogram of samples in which different per compounds with higher concentration and changed incubation time have been used (Table 3).
Figure 4:
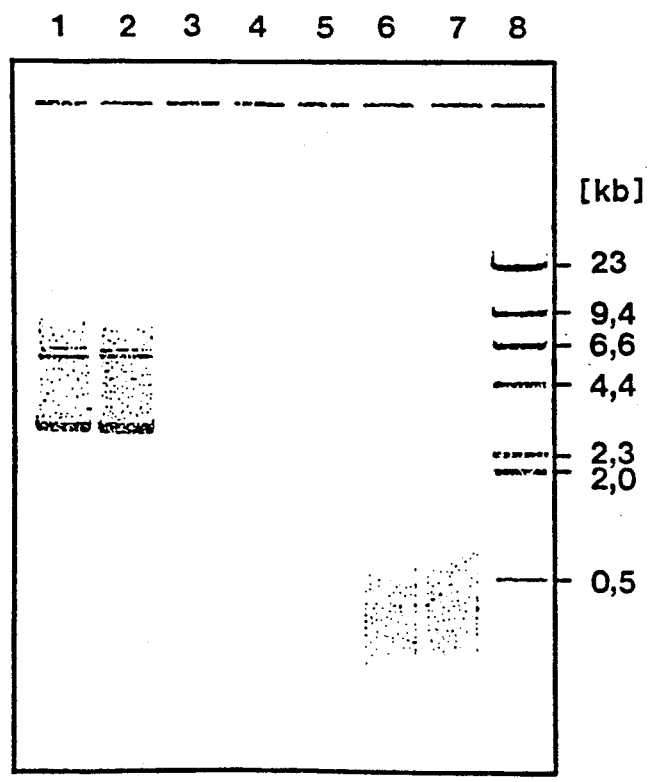
FIG. 4 shows an electropherogram of samples in which different peracetic acid concentrations have been used (Table 4).
Figure 5:
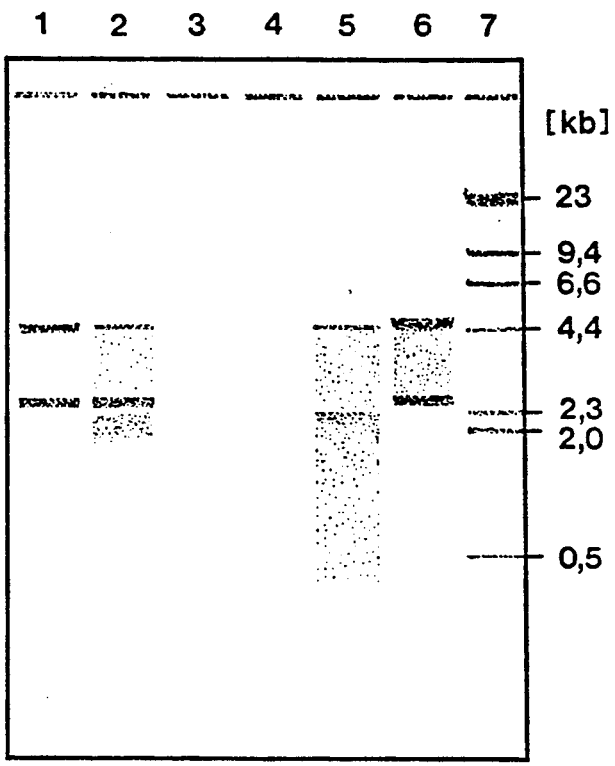
FIG. 5 shows an electropherogram of samples in which different concentrations of peroxomonosulphate have been used (Table 5).

The results are to be seen from the FIGS. 1 to 5. From FIGS. 1 and 2 it thereby follows that in the case of a concentration of 0.1% of per compound, in the case of an incubation time of 30 minutes and at a temperature of 80° C. only in the case of use of peracetic acid and sodium peroxide as per compound no DNA fragments with a length of over 500 base pairs (bp) are detectable. FIG. 3 shows that the use of peroxomonosulphate of a concentration of 0.5% gives a satisfactory fragmentation of the plasmid DNA. From FIG. 4 is to be seen that the use of peracetic acid with a concentration of 0.1% at a temperature of 80° C. and an incubation time of 30 minutes leads to a sufficient breakdown of the plasmid DNA, so that no fragments with a length of more than 500 base pairs are recognisable in the gel picture. FIG. 5 shows that in the case of the use of peroxomonosulphate with a concentration of 0.5% at a temperature of 80° C. and an incubation time of 30 minutes, a sufficient fragmentation of the plasmid DNA is also achieved.

EXAMPLE 2

Solutions of plasmid pBR322 were, as described in Example 1, incubated with 0.05% peracetic acid for 30 minutes at different temperatures. However, deviating from Example 1, instead of 30 μg. plasmid DNA/ml., 50 μg. plasmid DNA/ml. were used. The particular temperatures used are to be seen from the following Table 6:

TABLE 6

| trace | temperature |
|---|---|
| 1 | RT, without peracetic acid |
| 2 | 80° C., without peracetic acid |
| 3 | RT |
| 4 | 50° C. |
| 5 | 60° C. |
| 6 | 70° C. |
| 7 | 80° C. |
| 8 | λ-length standard |

Figure 6:
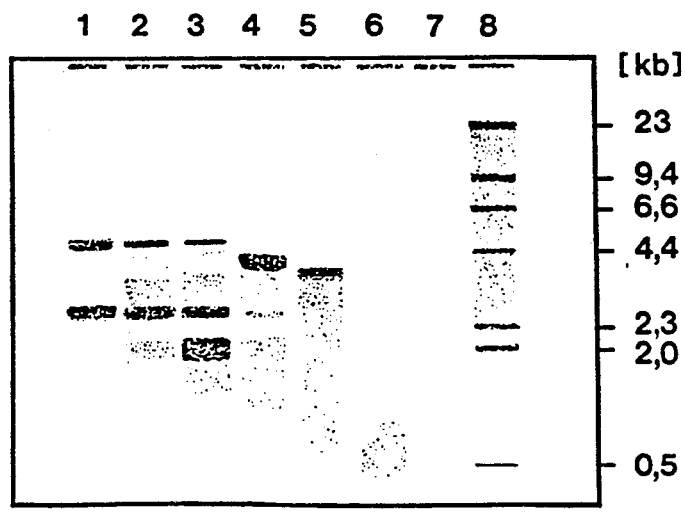
FIG. 6 shows an electropherogram of samples in which peracetic acid has been used at different temperatures (Table 6).

As described in Example 1, the solutions were then separated on an agarose gel electrophoresis plate. As comparison solutions were used 1 μg. pBR322 in 20 μl. TE buffer and 5 μl. sample buffer. The concentration of the length standard was analogous to Example 1. The results are to be seen from FIG. 6. It is thereby shown that in the case of an incubation time of 30 minutes, even at 60° C. a substantial fragmentation of the plasmid DNA is achieved and that at 70° C. no more fragments which are greater than 500 bp are recognisable in the gel picture.

EXAMPLE 3

The transformed micro-organism E. coli ED/pBT2a-I (DSM 3143) was fermentated as described in EP 187138. 0.1 ml. of culture broth were taken, incubated according to the invention at 80° C. for 30 minutes in different concentrations of peracetic acid and subsequently mixed with 10 μl. of a 10 mg./ml. proteinase K-containing solution and incubated at 37° C. for 30 minutes for the dissolving off of membrane-bound DNA. After centrifuging (Eppendorf centrifuge 14000 rpm/5 min.), in each case 20 μl. of this so treated culture broth was subjected to electrophoresis. The concentrations of the peracetic acid, as well as the particular incubation conditions used, are to be seen from the following Table 7:

TABLE 7

| trace | concentration of peracetic acid (wt. %) | temperature/ incubation time |
|---|---|---|
| 1 | centrifuged culture broth before incubation | |
| 2 | 0% | 80° C./30 min. |
| 3 | 0.1% | RT/2 hrs. |
| 4 | 0.1% | 80° C./30 min. |
| 5 | 0.2% | " |
| 6 | 0.5% | " |
| 7 | 1% | " |
| 8 | λ-length standard | — |

Figure 7:
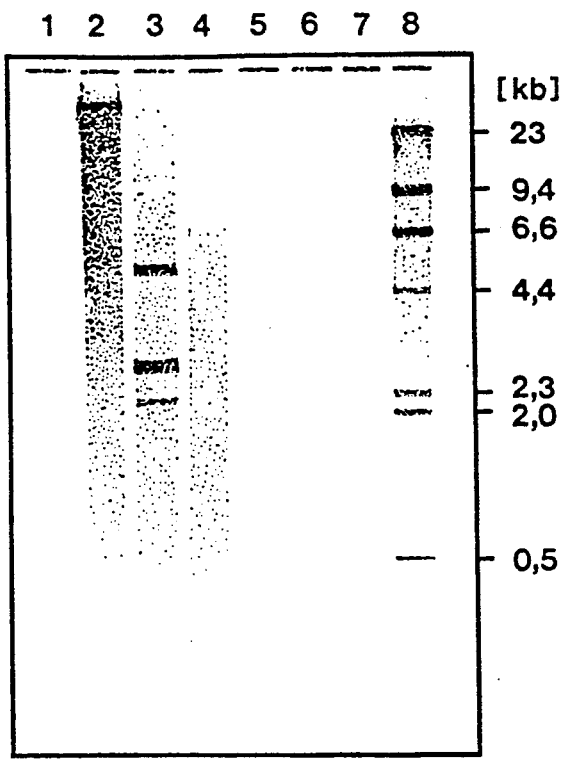
FIG. 7 shows an electropherogram of samples in which peracetic acid of different concentration has been used (Table 7).

The results are shown in FIG. 7. It is shown that also in a culture broth after treatment with 0.2% of peracetic acid in the case of an incubation time of 30 minutes and at a temperature of 80° C., no DNA fragments with more than 500 bp are detectable.

EXAMPLE 4 a) Inactivation of Eukaryotic Cells with Peracetic Acid

The hybridoma cells ECACC 84122003 were cultured as described in EP 150309. Solutions of these hybridoma cells were incubated with peracetic acid in various batches. The conditions are to be seen from the following Table 8:

TABLE 8

| trace | concentration of peracetic acid | temperature/ incubation time |
|---|---|---|
| 1 | 0% | room temperature |
| 2 | 0% | 80° C./30 min. |
| 3 | 0.2% | 80° C./30 min |

Figure 8:
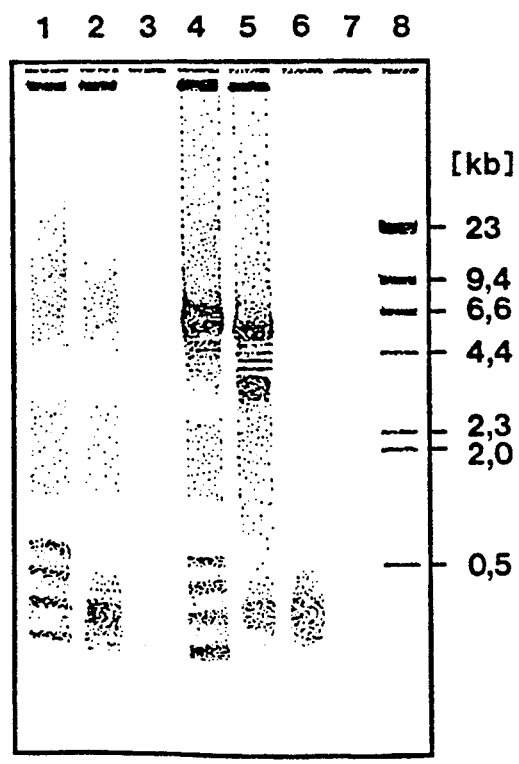
FIG. 8 shows an electropherogram of samples of DNA of a eukaryotic cell line which has been treated with peracetic acid (Table 8 and 9).

As samples 1 to 3, in each case 20 μl. of a suspension of $10^7$ cells/100 μl. were applied to agarose gel electrophoresis plates and separated. The result is illustrated in FIG. 8. It is shown that the treatment with peracetic acid of a concentration of 0.2% at an incubation temperature of 80° C. and an incubation period of 30 minutes so destroys the DNA that no DNA fragments with a length of over 500 bp are any longer detectable.

b) Testing of the Transformation Ability of pBR322 in the Presence of Eukaryotic Cells After Treatment with Peracetic Acid As sample solutions were used suspensions of $10^7$ of the hybridoma cells obtained according to a) per 0.1 ml. which additionally contained 5 μg. pBR322/0.1 ml. These solutions were treated with peracetic acid. The incubation conditions are to be seen from the following Table 9:

TABLE 9

| trace | concentration of peracetic acid | temperature/ incubation time |
|---|---|---|
| 4 | 0% | room temperature |
| 5 | 0% | 80° C./30 min. |
| 6 | 0.2% | " |
| 7 | 1% | " |
| 8 | λ-length standard | — |

In each case, 20 μl. of these mixtures were separated by agarose gel electrophoresis. The results are to be seen from FIG. 8. It is shown that peracetic acid of a concentration of 0.2% in the case of an incubation time of 30 minutes and an incubation temperature of 80° C. leads to a satisfactory destruction of the DNA so that no DNA fragments with more than 500 bp are any longer contained.

Of the samples 4 to 7 prepared according to b), after the incubation with peracetic acid, in each case a part was dialysed against TE buffer, pH 7.5. Of the hereby obtained solutions, in each case 20 μl. were transformed by a transformation of E. coli HB101 (DSM 1607) via the calcium chloride method described by Maniatis "Molecular Cloning", pages 250-251.

The conditions used, as well as the living germ counts (LGC) obtained, are to be seen from the following Table 10:

TABLE 10

| | | incubation conditions | | | |
|---|---|---|---|---|---|
| sample | cell type | peracetic acid | temperature | time | LGC |
| 1 | pBR322[a)] | 0 | — | — | $1.4 \times 10^6$ |
| 2 | cell culture solution[b)] | 0 | RT | — | $1 \times 10^3$ |
| 3 | cell culture solution[b)] | 0 | 80° C. | 30 min. | $5 \times 10^5$ |
| 4 | cell culture solution[b)] | 0.2% | 80° C. | 30 min. | 0 |
| 5 | cell culture | 1% | 80° C. | 30 min. | 0 |

TABLE 10-continued

| | | incubation conditions | | | |
|---|---|---|---|---|---|
| sample | cell type | peracetic acid | temperature | time | LGC |
| | solution[b] | | | | |

[a]pure plasmid solution 1 μg. in 20 μl. TE buffer, pH 7.5
[b]plasmid in cell culture solution (partly digested by nucleases; dialysed; 20 μl. thereof transformed in E. coli).

For the determination of the LGC, the solutions containing the bacteria in $10^{-1}$ to $10^6$ fold dilution were plated out on agar plates with LB medium with and without ampicillin (50 μg./ml.), cultured overnight at 37° C. and subsequently the number of grown colonies determined visually.

It is shown that the incubation with 0.2% peracetic acid in the case of an incubation temperature of 80° C. and an incubation period of 30 minutes leads to a complete killing off of the cells.

We claim:

1. A method for the breakdown and inactivation of the biological activity of natural and recombinant DNA comprising adding to a DNA-containing biomass a peroxy compound in an amount range of about 0.05 to 5% selected from the group consisting of a $C_1$–$C_3$ percarboxylic acid or a salt thereof, an ammonium or an alkali metal peroxide and an ammonium or an alkali metal peroxomonosulphate and subsequently heating the mixture to 60° to 100° C. until DNA with a chain length of more than 500 base pairs is not detectable chromatographically, and thereby breaking down the peroxy compounds resulting in biologically harmless and non-toxic compounds.

2. The method of claim 1 comprising inactivating at a pH value in the range of 6 to 11.

3. The method of claim 2 comprising inactivating at a pH value in the range of 7 to 10.

4. The method of claim 1 comprising the use of a percarboxylic acid selected from the group consisting of peracetic, performic, perproprionic acid or a salt thereof.

5. The method of claims 1, 2 or 3 comprising adding a Na, K or Li alkali metal compound.

6. The method of claims 1, 2 or 3 comprising inactivating recombinant DNA.

* * * * *